United States Patent [19]
Rhodes

[11] Patent Number: 5,078,985
[45] Date of Patent: Jan. 7, 1992

[54] RADIOLABELING ANTIBODIES AND OTHER PROTEINS WITH TECHNETIUM OR RHENIUM BY REGULATED REDUCTION

[75] Inventor: Buck A. Rhodes, Albuquerque, N. Mex.

[73] Assignee: RhoMed, Incorporated, Albuquerque, N. Mex.

[21] Appl. No.: 391,474

[22] Filed: Aug. 9, 1989

[51] Int. Cl.$^5$ .......................................... A61K 39/395
[52] U.S. Cl. .................................. 424/1.1; 530/387; 530/388; 530/402
[58] Field of Search ................ 424/1.1; 530/388, 389, 530/363, 402, 382, 395

[56] References Cited

U.S. PATENT DOCUMENTS

| | | | |
|---|---|---|---|
| 4,305,922 | 12/1981 | Rhodes | 424/1 |
| 4,311,688 | 1/1982 | Burchiel et al. | 424/1 |
| 4,323,546 | 4/1982 | Crockford et al. | 424/1 |
| 4,331,647 | 5/1982 | Goldenberg | 424/1 |
| 4,348,376 | 9/1982 | Goldenberg | 424/1 |
| 4,421,735 | 12/1983 | Haber et al. | 424/1.1 |
| 4,424,200 | 1/1984 | Crockford et al. | 424/1.1 |
| 4,472,371 | 9/1984 | Burchiel et al. | 424/1.1 |
| 4,478,815 | 10/1984 | Burchiel et al. | 424/1.1 |
| 4,479,930 | 10/1984 | Hnatowich | 424/1.1 |
| 4,647,445 | 3/1987 | Lees | 424/1.1 |
| 4,652,440 | 3/1987 | Paik et al. | 424/1.1 |
| 4,668,503 | 5/1987 | Hnatowich | 424/1.1 |
| 4,670,545 | 6/1987 | Fritzberg et al. | 534/14 |
| 4,877,868 | 10/1989 | Reno | 530/390 |

FOREIGN PATENT DOCUMENTS

| | | |
|---|---|---|
| 0237150 | 9/1987 | European Pat. Off. |
| 0271806 | 12/1987 | European Pat. Off. |
| 0336678 | 4/1989 | European Pat. Off. |
| 85/03231 | 8/1985 | PCT Int'l Appl. |
| 87/04164 | 7/1987 | PCT Int'l Appl. |
| WO88/07382 | 10/1988 | PCT Int'l Appl. |

OTHER PUBLICATIONS

"Three Approaches to Radiolabeling antibodies with 99mTc" by W. C. Eckelman et al., *Nucl. Med. Biol.*, vol. 16, No. 2, pp. 171-176 (1989).

"A New Method for Protein Labeling with 99mTc" by D. Blok et al., *Nucl. Med. Biol.*, vol. 16, No. 1, pp. 11-16 (1989).

"Covalent Attachment of Chelating Groups to Macromolecules" by G. E. Krejcarek et al., *Biochemical and Biophysical Research Communications*, vol. 77, pp. 581-585 (1977).

"'Bifunctional' Chelating Agents for Binding Metal Ions to Proteins" by T. G. Wensel, et al., *Radioimmunoimaging and Radioimmunotherapy*, pp. 185-196 (1983).

"99m TC Labeling of Proteins: Initial Evaluation of a Novel Diaminedithiol Bifunctional Chelating Agent" by K. E. Baidoo, *Cancer Research*, vol. 50, pp. 799-802 (1990).

"Radioimmunoimaging of Experimental Thrombi in Dogs Using Technetium-99-m Labeled Monoclonal Antibody Fragments Reactive with Human Platelets" by P. Som, et al., *Journal of Nuclear Medicine*, vol. 27, No. 8, pp. 1315-1320 (1986).

"Technetium-99m-Albumin" by H. S. Stern, et al., Book Chapter published by Johns Hopkins Medical Institutions, Baltimore, MD, pp. 359-375 (U.S. Atomic Energy Commission) (1966).

"Use of Fe(II) or Sn(II) Alone for TEchnetium Labeling of Albumin" by M. S. Lin, et al., *Journal of Nuclear Medicine*, vol. 12, pp. 204-211 (1971).

"99m Tc-Human Serum Albumin" by W. C. Eckelman, et al., *Journal of Nuclear Medicine*, vol. 12, pp. 707-710 (1971).

"A Rapid Chemical Method of Labeling Human Plasma Proteins with 99m Tc-Pertechnetate at pH 7.4" by D. W. Wong et al., *Journal of Applied Radiation and Isotopes*, vol. 29, pp. 251-253.

"A Rapid Method for Labeling IgG with 99m" by L. G. Colombetti et al., Abstract from *Journal of Nuclear Medicine*, Proceedings of 26th Annual Meeting, p. 652 (1979).

"A Novel Approach to Tc-99m-Labeled Monoclonal Antibodies" by A. Schwarz et al., *Proceedings of 34th Annual Meeting*, vol. 28, No. 4, pp. 721 (1987).

"A Rapid and Efficient Method for Labeling IgG Antibodies with Tc-99m and Comparison to Tc-99m FAB' Antibody Fragments" by K. Y. Pak et al., Abstract from *Proceedings of the 36th Annual Meeting*, vol. 30, No. 5, p. 793 (1989).

"Imaging of Inflammatory Arthritis with Technetium-99m-Labeled IgG" by F. Breedveld et al., *Journal of Nuclear Medicine*, pp. 2017-2021 (1989).

(List continued on next page.)

[57] ABSTRACT

Proteins are radiolabeled with radionuclides of technetium or rhenium by a process in which the disulfide bonds of the protein are first partially reduced with stannous salts or other disulfide reducing agents, all substances other than the desired reduced protein removed, by size exclusion chromatography or other purification means, and a specified, smaller amount of pertechnetate or perrhenate reducing agent, such as a stannous salt, is added to the reduced protein in a manner such that further reduction of the protein is limited. Pertechnetate or perrhenate is then added to the mixture of the reduced protein and the pertechnetate or perrhenate reducing agent; the pertechnetate or perrhenate is reduced and becomes strongly bonded to the protein via the sulfhydryl groups previously exposed by reduction of disulfide groups. The reduced protein and pertechnetate or perrhenate reducing agent can be idefinitely stored frozen or lyophilized.

18 Claims, No Drawings

*Primary Examiner*—John S. Maples
*Attorney, Agent, or Firm*—Deborah A. Peacock

OTHER PUBLICATIONS

"Coupling of the 99m Technetium-Nitrido Group to Monoclonal Antibody and Use of the Complexes for the Detection of Tumors in Mice" by J. Kanellos, *JNCI*, vol. 77, No. 2, pp. 431–439 (1986).

"Technetium-99m Labeling of Murine Monoclonal Antibody Fragments" by Rhodes et al. *Journal of Nuclear Medicine*, vol. 27, No. 5 (1986, pp. 685–693.

"Technetium-99m Labeling of Murine Monoclona Antibody Fragments" by Buck A. Rhodes et al., *Journal, Nucl. Med.*, vol. 27, pp. 685–693 (1987).

"Radioimmunoimaging of Experimental Thrombi in Dogs Using Technetium 99m Labeled Monoclonal Antibody Fragments Reactive with Human Platelets" by P. Som et al., *Journal, Nucl Med.*, vol. 27, pp. 1315–1320 (1986).

"A Novel Approach to TC-99m Labelled Monoclonal Antibodies" by A. Schwarz and A. Steinstraber Hoechst, *Journal Nucl. Med.*, vol. 28, p. 721 (1987).

"A Rapid and Efficient Method for Labeling IgG Antibodies with TC-99m FAB' Antibody Fragments" by K. Y. Pak et al., *Journal Nucl. Med.*, vol. 30, p. 793 (1989).

"A TC-99m Labelled Monoclonal Antibody PR1A3 for Radioimmunoscintigraphy, RIS of Colorectal Cancer" by M. Granowska et al., *Journal Nucl. Med.*, vol. 30, p. 748 (1989).

RADIOLABELING ANTIBODIES AND OTHER PROTEINS WITH TECHNETIUM OR RHENIUM BY REGULATED REDUCTION

BACKGROUND OF THE INVENTION

1. Field of the Invention

This invention relates to a method, composition and kit for radiolabeling proteins with radioisotopes of technetium and rhenium such as technetium-99m.

2. Description of the Prior Art

The use of radioisotopes to label proteins is well known. These compositions can be used in assays, and can be administered to the human body to visualize or monitor functioning of various parts of the body or to determine the presence and location of particular antigens, antibodies, hormones and the like. A variety of radioisotopes, including isotopes of iodine, technetium, indium, and rhenium have been used. It is also well known that protein molecules can be tagged or labeled with technetium-99m to form a diagnostic or imaging agent.

Technetium-99m has been utilized to radiolabel proteins, chelating agents, phosphonate bone scanning compositions and the like by a technique which utilizes sodium pertechnetate wherein the technetium initially is in the +7 state. Technetium-99m is generally available only as sodium pertechnetate. The pertechnetate must be contacted with a reducing agent, such as stannous chloride, in order to reduce the technetium to the +3, +4 or +5 oxidation state in the presence of the protein, chelating agent or like substance which is to be radiolabeled. The technetium must be maintained in this reduced state in order to maintain the chemical bond between the technetium molecule and the substrate being radiolabeled. It is also necessary that the technetium be firmly bound to the protein such that the reduced technetium is not transferred to other molecules or other proteins present in the assay, patient's blood or other media in which the radiolabeled substance will be utilized.

Several different methods have been utilized to radiolabel proteins, particularly monoclonal antibodies, with technetium-99m. The methods involve two general approaches. One approach is indirect in which a bifunctional chelating agent is attached to the protein via one functional group and the technetium-99m is attached via the other functional, or chelating, group. This method was introduced by Krejcarek GE and Tucker KL (*Biophys Res Comm* 77:581-585, 1977) and has been widely employed in many variations using a wide variety of bifunctional chelating agents such as described in the review of Wensel and Meares (Wensel TG and Meares CF: "Bifunctional" Chelating Agents for Binding Metal Ions to Proteins, in Radioimmunoimaging and Radioimmunotherapg, SW Burchiel and BA Rhodes, eds., Elsevier Publishing Co., N.Y., 1983, pp 185-196). Other methods are disclosed by Hnatowich, U.S. Pat. Nos. 4,668,503 and 4,479,930, by Haber et al., U.S. Pat. No. 4,421,735 and by Fritzberg et al., U.S. Pat. No. 4,670,545. The bifunctional chelate methods all present significant limitations, including the complexity of the radiolabeling procedure, the time required to accomplish radiolabeling, and the presence of substances which may affect the protein.

The other general approach is direct labeling. Although several direct methods have been reported, the first direct method capable of providing a sufficiently strong bond between the protein and the technetium-99m for in vivo applications was the direct or pretinning method described in U.S. Pat. No. 4,424,200, entitled "METHOD FOR RADIOLABELING PROTEINS WITH TECHNETIUM-99M", to Crockford and Rhodes. In this method, a single reduction compound, consisting of a solution of stannous chloride and other salts which serves both to reduce the protein, thereby exposing the disulfide bonds, and to reduce the sodium pertechnetate, is used. With this method, many proteins can be successfully radiolabeled with technetium-99m. Several investigators have reported on the use of this method (Rhodes BA et al: "Technetium-99m labeling of murine monoclonal antibody fragments. J Nucl Med 27:685-693, 1986; Som P et al: Radioimmunoimaging of experimental thrombi in dogs using technetium-99m-labeled monoclonal antibody fragments reactive with human platelets. J Nucl Med 27:1315-1320, 1987) and on equivalent methods (Schwarz A and Steinstruaber A: A novel approach to Tc-99m-labeled monoclonal antibodies. J Nucl Med 28:721, 1987; Pak KY et al: A rapid and efficient method for labeling IgG antibodies with Tc-99m and comparison to Tc-99m Fab'. J Nucl Med 30:793, 1989; Granowska M et al: A Tc-99m-labeled monoclonal antibody, PR1A3, for radioimmunoscintigraphy. J Nucl Med 30:748, 1989). In the equivalent methods disulfide reducing agents other than stannous salts were used. Pak et al used dithiothreitol to reduce the disulfide bonds of the antibody; Swartz and Steinsbruaber, and Granowska et al used 2-mercaptoethanol. Also some of these investigators (Swartz and Steinsbruaber,. and Granowska et al) reduced the Tc-99m prior to adding it to the reduced antibody, which adds steps to the original procedure.

However, certain proteins, such as some monoclonal antibodies or fragments thereof, cannot be successfully labeled using the previously described direct method or its equivalents. This is primarily due to problems associated with lack of purity of the protein, continued reduction of disulfide bonds in the protein, and the formation of additional reduced protein species prior to admixture with sodium pertechnetate. Fewer stannous ions are needed to reduce pertechnetate than to reduce disulfide bonds in proteins; with some proteins, excess stannous ions cause reduction of disulfide bonds and fragmentation of the protein to less than the desired size. Organic reducing agents such as 2-mercaptoethanol and dithiothreitol can cause aggregation of the reduced antibody or antibody fragments.

Accordingly, it is an object of the present invention to provide an improvement over the previous methods for direct labeling of proteins with technetium-99m, which method will eliminate undesirable fragments or otherwise degraded protein components from the final product.

It is a further object of the present invention to provide a method which will result in increased radiolabeling efficiencies utilizing technetium-99m as the radioisotope.

Another object of the present invention is to provide a method and kit which will permit radiolabeling to be accomplished by the end user using a single vial, containing both reduced antibody and stannous ions, and further containing a means to maintain low quantities of stannous ions while protecting against oxidation loss, which method requires only a single step to accomplish radiolabeling, being the introduction of sodium pertechnetate.

Other objects and the further scope of applicability will become apparent from the detailed description to follow.

SUMMARY OF THE INVENTION

In accordance with the present invention, a method is provided for radiolabeling proteins with technetium-99m in which a reducing agent is used to reduce the disulfide bonds in the protein, the reducing agent and any impurities are removed, and a low concentration and limited amount of pertechnetate reducing agent added to reduce the sodium pertechnetate.

A protein substrate to be radiolabeled is admixed with a solution of stannous chloride composition having a pH between about 4.5 and about 8.5, and preferably about pH 5.6, the solution being further composed of a mixture of sodium potassium tartrate and potassium hydrogen phthalate, the pH adjusted to approximately $5.6 \pm 0.05$ using sodium hydroxide, and the resulting solution purged of oxygen. Alternatively, the solution may include other salts such as sodium chloride, sodium acetate, gentisic acid, or stannous fluoride. The stannous chloride solution is added to the protein in an oxygen free environment, and the protein and stannous chloride solution allowed to incubate for several hours (usually twenty-one hours) in the absence of oxygen and at room temperature. Alternately higher or lower incubation temperatures may be used with a corresponding inverse change in the incubation time, such that if the incubation temperature is increased, the incubation time is decreased, and vice versa. For certain proteins, such as some monoclonal antibodies, the reaction time may be shortened to less than 21 hours to prevent excessive fragment of the antibody protein.

Following incubation, the protein and stannous chloride solution is either frozen to stop the reduction reaction, or is immediately purified by size exclusion chromatography using an appropriate gel in a column equilibrated with phosphate buffered saline. The protein and buffered stannous chloride solution is loaded into the column, and eluted using phosphate buffered saline, with the molecular weights of the eluant monitored and relevant fractions collected. The fractions corresponding to the protein to be radiolabeled are collected and pooled, and concentrated by ultrafiltration. Alternatively, the protein may be purified by any other suitable method including such methods as dialysis, ultrafiltration, precipitation, preparative high performance liquid chromatography, affinity chromatography, other forms of chromatography or preparative isoelectric focusing. The resulting protein, substantially free of the stannous chloride solution and contaminants or proteins of molecular weight other than the protein to be radiolabeled, can then be frozen in an oxygen free vial.

To the oxygen free vial containing the frozen purified and reduced protein, a solution capable of reducing sodium pertechnetate in saline solution is added in a manner to prevent immediate admixing of the two solutions. A pure tin pellet can also be added to each vial. The resulting combination is prepared as layers of frozen solutions or is otherwise prepared without allowing any reaction between the frozen, purified, and reduced protein and the solution for reducing the sodium pertechnetate. A carrier protein may also be added to protect against radiolysis of the purified and reduced protein, and to prevent adhesion of the purified and reduced protein to surfaces, such as the vial wall. A layer of carrier protein, such as non-reduced human serum albumin or another inert diluent such as inositol or another inert sugar, is added, and the layer is frozen or otherwise prepared without allowing any admixture with the other solutions until use. Oxygen is excluded from the vial containing the two unmixed solutions. The vial is stored frozen or it is lyophilized and stored for subsequent reconstitution when radiolabeling is desired. The solution for reducing the sodium pertechnetate may be composed of stannous chloride and a mixture of sodium potassium tartrate and potassium hydrogen phthalate, the pH adjusted to approximately $5.6 \pm 0.05$ using sodium hydroxide, and the resulting solution purged of oxygen. In practice, frequently the same solution can be used to reduce both the protein and the sodium pertechnetate; however, the amount or concentration of stannous salts used to reduce the sodium pertechnetate is substantially less than the amount or concentration used to reduce the protein. Alternatively, the solution used for reducing the sodium pertechnetate can be composed of any substance which effectively reduces sodium pertechnetate and does not alter the protein to be radiolabeled, such as such as stannous phosphonate, stannous gluconate, or stannous glucoheptonate. No more of the pertechnetate reducing solution than is required to reduce the sodium pertechnetate is used. This is done to prevent possible degradation of the protein, primarily by further cleavage of disulfide bonds due to the action of the pertechnetate reducing reagent.

Solid, highly pure metallic tin may be added to the vial, generally at or after freezing, and in the form of a non-oxidized tin pellet. The addition of metallic tin prevents oxidation loss during storage and reconstitution.

The resulting frozen or lyophilized combination of purified, reduced or pretinned protein and the pertechnetate reducing solution, together with the tin pellet, carrier protein and other inert diluents, is admixed with sodium pertechnetate-Tc-99m solution while avoiding the introduction of oxygen. The admixture is then incubated for a period (usually fifteen minutes) at room temperature to allow for the reduction of the technetium and its binding to reduced protein. The admixture may be stabilized by the addition of human serum albumin or other similar protein in normal saline, if a carrier protein was not included in the original vial.

This thus provides a method for radiolabeling proteins containing sulfhydryl groups with radionuclides of technetium or rhenium to obtain stable labeling, by incubating the protein with a first reducing agent to partially reduce the disulfide bonds, purifying the reduced protein to remove the first reducing agent and all impurities, and adding only so much of a second reducing agent as is necessary to reduce pertechnetate or perrhenate. A preferred first reducing agent is a source of stannous ion in a solution composed of a mixture of an alkali metal biphthalate and an alkali metal tartrate having a pH between about 5.0 and 6.0. The first reducing agent may also be 2-mercaptoethanol, 1,4 dithiothreitol, 2,3 dihydroxybutane-1, 4 dithiol, 2-aminoethanethiol HCl, 2-mercaptoethylamine, thioglycolate, cyanide, cysteine or other substances capable of reducing disulfide bonds. A preferred second reducing agent is a source of stannous ion in a solution composed of a mixture of an alkali metal biphthalate and an alkali metal tartrate having a pH between about 5.0 and 6.0. The second reducing agent may also be stannous glucoheptonate, stannous phosphonate, dithionite or other substances capable of reducing pertechnetate or perrhenate. Following the purification of the protein combination, the purified protein combination can be frozen, the second reducing agent added, and the second reducing agent immediately frozen so that no chemical reaction occurs between the purified protein combination and second reducing agent prior to thawing for use. It is also possible, following the freezing of the protein combination and the second reducing agent, to lyophilize the composition. At or subsequent to the addition of the second reducing agent, solid, non-oxidized metallic tin can be added to the combination of the protein combination and the second reducing agent. Purification may be accomplished by passage of the protein combination through a size exclusion chromatography column, or by methods such as use of a desalting column, dialysis, ultrafiltration, precipitation, preparative high performance liquid chromatography, affinity chromatography, or preparative isoelectric focusing. Optimal results are obtained when the concentration of the protein in the protein combination and second reducing agent is at least 1 milligram per milliliter of solution, and the volume of the protein combination and second reducing agent is at least 2 milliliters.

This invention provides for a composition suitable for use in preparing a protein having a stable label of a radionuclide of technetium or rhenium, which composition is composed of a protein which has been reduced so that the sulfhydryl groups are exposed, so much of a stannous ion-containing reducing compound for pertechnetate or perrhenate as will reduce the pertechnetate or perrhenate without further reduction of the protein, and pure, non-oxidized metallic tin. The source of pure, non-oxidized metallic tin may be a tin pellet. The composition may be made using a reduced antibody or antibody fragment as the reduced protein. An inert carrier substance may also be added to the composition, such as an inert sugar or non-reduced inert protein. The composition may be lyophilized, preferably buffered at a pH of 4–6.

A kit is also provided which includes the frozen or lyophilized combination of purified and pretinned protein and the pertechnetate reducing solution in a single oxygen purged vial, together with stabilizing agents, if required, ready for radiolabeling.

DESCRIPTION OF SPECIFIC EMBODIMENTS

The stannous chloride reducing agent is prepared by dissolving stannous chloride crystals in concentrated hydrochloric acid at 0.5 M, yielding approximately 94.8 mg of stannous chloride per ml. This solution is then stored in sealed and nitrogen purged vials until used. Alternate sources for stannous chloride can be used, including use of a non-oxidized solid tin pellet contacted with concentrated hydrochloric acid.

A tartrate-phthalate solution which comprises a mixture of sodium potassium tartrate and potassium hydrogen phthalate is prepared. 0.282 g of sodium potassium tartrate is dissolved in 100 ml of distilled water, and to this is added 0.817 g potassium hydrogen phthalate. The pH is adjusted to approximately 5.0, using 10N sodium hydroxide, and is then adjusted to 5.6±0.05 using 1N sodium hydroxide. The resulting solution is stirred and purged of oxygen by bubbling an inert gas, such as nitrogen, helium or the like, through the substance.

The pretinning solution is made by measuring a portion of the purged tartrate-phthalate solution into a flask, and slowly adding thereto a volume of the stannous chloride. It is preferable if a stir bar or similar mechanism is used to insure mixture of the stannous chloride as it is added to the buffer. Approximately one volume of stannous chloride to 100 volumes of buffer is used. The pH is continuously monitored, and once the stannous chloride has been added, the pH is adjusted to approximated 5.0, using 10N sodium hydroxide, and is then adjusted to 5.6±0.05 using 1N sodium hydroxide. All steps are undertaken in an oxygen free environment, and may be done while bubbling an inert gas through the solution. The resulting solution is purged of oxygen by bubbling an inert gas, such as nitrogen, helium or the like, through the substance.

Alternately, the antibody reducing solution can be made using other disulfide reducing agents such as 2-mercaptoethanol, 1,4 dithiothreitol, 2,3 dihydroxybutane-1, 4 dithiol, 2-aminoethanethiol HCl, 2-mercaptoethylamine, thioglycolate, cyanide, cysteine, or other disulfide splitting reagents.

The protein to be reduced is placed in a nitrogen purged, sealed vial. If monoclonal antibody or fragments thereof are to be labeled, a minimum of 0.1 mg, and preferably at least 2 mg of monoclonal antibody or fragments is used, at a concentration of 1 mg or more per ml, preferable 1.7 mg/ml. The monoclonal antibody, fragments or other protein may be diluted in normal saline, or concentrated by ultrafiltration, as may be necessary. To the protein, pretinning solution is added, in the approximate ratio of 3 volumes of protein to 2 volumes of pretinning solution. The vial containing the protein and pretinning solution is then allowed to incubate, preferably in an oxygen free environment, such as a container filled with nitrogen or another inert gas. The vial is allowed to incubate at room temperature for a period sufficient to allow reduction of the disulfide bonds in the protein. Generally, incubation for between fifteen and twenty-four hours at room temperature is adequate, with incubation for twenty-one hours at room temperature being preferred for most immunoglobulins. If the temperature is increased, the incubation time is decreased, and conversely, incubation at lower temperatures requires correspondingly longer incubation times. Incubation is terminated by freezing the admixture of protein and pretinning solution, or by proceeding immediately to purification.

When other reducing agents are used, such as 2-mercaptoethanol, 1,4 dithiothreitol, 2,3 dihydroxybutane-1,4 dithiol, 2-aminoethanethiol HCl, 2-mercaptoethylamine, thioglycolate, cyanide, cysteine, or other disulfide splitting reagents, the incubation time must be adjusted for the specific reducing agent being used. Generally, a shorter incubation time is required.

The admixture of protein and pretinning or other reducing solution is purified by size exclusion chromatography. A column is packed with an appropriate gel, such as Sephacryl-200 gel (Pharmacia, Piscataway, N.J.) for use with low molecular weight monoclonal antibody F(ab')$_2$ fragments. The column is equilibrated with an appropriate elution buffer, such as phosphate buffered saline. The admixture of protein and reducing solution is applied to the column and fractionated, using the elution buffer. A fraction profile is generated using an ultraviolet detector or similar device, and the fractions containing the resulting protein to be radiolabeled are collected and pooled. The resulting reduced protein is concentrated, if necessary, preferably to a concentration of 1.7 mg/ml. Concentration can be accomplished by ultrafiltration. The resulting concentrate can also be dialyzed against normal saline to remove any residual stannous salts or other residual reducing agent.

Alternately, the admixture of pretinned protein and pretinning or other reducing solution may be purified by passage of the admixture through a desalting column, and collecting the reduced protein and discarding the stannous salts or other excess reducing reagents. The resulting eluant can be concentrated and dialyzed as required. This method will remove pretinning solution and other reducing reagents, but will not necessarily remove other impurities, such as smaller fragments of the protein resulting from over reduction of the disulfide bonds in the protein or aggregation of reduced proteins. These small fragments or large aggregates, in the case of monoclonal antibodies, may not be immunoreactive, or may have a biodistribution different than than of the desired protein, necessitating their removal from the final product.

Alternately, the admixture of reduced protein and pretinning or other reducing solution may also be purified by other means, including dialysis, ultrafiltration, precipitation, preparative high performance liquid chromatography, affinity chromatography, other forms of chromatography, and preparative isoelectric focusing.

The purified, reduced protein is then purged of oxygen, preferably by bubbling an inert gas such as nitrogen through the solution, and can be frozen in oxygen-purged vials. To each vial containing frozen protein solution, pertechnetate reducing solution is added, and the contents either immediately frozen or lyophilized, so that no reaction takes place between the frozen protein solution and the pertechnetate reducing solution. A non-oxidized tin pellet may also be added to the vial, which tin pellet will replace trace amounts of $Sn^{+2}$ and help to stabilize the low concentration of stannous ions in the pertechnetate reducing solution, and to help prevent losses of radiolabel due to reoxidation during storage of the radiolabeled product. The pertechnetate reducing solution can be made as the pretinning solution was made, except that approximately one volume of stannous chloride at 0.5M is added to approximately 5,000 volumes of tartrate-phthalate solution, resulting in a pertechnetate reducing solution of approximately 0.1 millimolar. Approximately one volume of pertechnetate reducing solution is added to two volumes of purified, reduced protein. Optimally, the purified, reduced protein solution is at a concentration of approximately 1.7 mg/ml, and to each 1.32 ml of the purified, reduced protein solution, approximately 0.68 ml of pertechnetate reducing solution is added.

Alternately, the pertechnetate reducing solution can be made using stannous glucoheptonate, stannous phosphonate, dithionite and other commonly used Tc-99m radiopharmaceutical kits.

The pertechnetate reducing solution can also be used to reduce perrhenate.

To radiolabel, the desired activity of sodium pertechnetate-Tc-99m is added and admixed, and the admixture allowed to incubate for a period, generally approximately fifteen minutes. This step is conducted while avoiding or minimizing the introduction of atmospheric oxygen. If desired, the resultant radiolabeled protein can be stabilized by the addition of 1% human serum albumin in normal saline or other suitable protective protein.

The source of technetium-99m is conventionally obtained as sodium pertechnetate-Tc-99m from a 99Mo/99mTc generator. Any source of pharmaceutically acceptable technetium-99m may be utilized in the present invention.

Alternatively other radioisotopes of technetium and isotopes of rhenium such as Re-186 and Re-188 may be used. When perrhenate rather than pertechnetate is reduced usually a higher temperature and a longer radiolabeling time is required to carry the reaction to completion.

Any protein, chelating agent or other substrate which contains disulfide bonds which can be reduced can be radiolabeled in accordance with this invention. Representative suitable substrates include IgG, IgM, Fab' and F(ab')₂ fragments of IgG, fragments of IgM, human serum albumin, fibrinogen, urokinase, gamma globulin, and other proteins.

The present invention, through inclusion of the purification step, and concomitant removal of the excess reducing reagents, presents a number of significant advantages. By removal of all species of reduced protein other than the protein to be radiolabeled, including smaller or larger molecular weight species, competition for reduced Tc-99m is eliminated. This results in significantly higher radiolabeling yields. By keeping the total amount of stannous and stannic ions in the pertechnetate reducing solution as low as possible, the formation of additional reduced protein species is minimized. It generally takes far fewer stannous ions to reduce pertechnetate than to reduce the disulfide bonds in proteins, thereby allowing reduction of pertechnetate without additional reduction of disulfide bonds in the protein to be radiolabeled, which additional reduction could result in protein species other than protein to be radiolabeled.

The present invention also presents significant advantages because it requires only one step to accomplish radiolabeling by the end user, the addition of sodium pertechnetate and the concomitant incubation thereof. This significant simplification is possible because both the stannous ions and the reduced antibody are frozen, together with a carrier protein and other inert diluents, and optionally lyophilized, in the same vial. The addition of the tin pellet, or other source of purified and non-oxidized metallic tin, further preserves the low concentration of stannous ions and helps prevent loss of radiolabel due to oxidation during storage or reconstitution.

The following examples illustrate the present invention and are not intended to limit the same.

EXAMPLE I

This example illustrates the process of this invention for labeling immunoglobulin G (IgG). IgG is obtained obtained from animals such as sheep, goats, mice or humans. Sodium Pertechnetate-Tc-99m U.S.P. is obtained from any commercial source. To 20 ml of a 40 mM potassium biphthalate and 10 mM sodium tartrate solution (pH 5.6) was added 0.2 ml of 0.5 M stannous chloride in concentrated HCl (12 M). The stannous chloride was prepared by adding the concentrated hydrochloric acid to non-oxidized pellets of $SnCl_2$ having a surface free of dull stannous oxide. The pH of the resultant reducing solution then was brought up to 5.6±0.05, by adding 10 M NaOH to pH 5.5, and adding 1 M NaOH to adjust to the final pH. An IgG preparation was made by diluting 0.25 ml of Immune Globulin (Human), U.S.P., Cutter Biological, which contained 15-18% protein stabilized with 0.21-0.32 M glycine, with 7.25 ml of Sterile Water for Injection, U.S.P., and filtering through a 0.22 micron filter. 5 ml of the reducing solution was mixed with 7.5 ml of the IgG preparation. The vial containing the admixed solutions was sealed and flushed with $N_2$ gas to remove oxygen. This admixed solution was stored for 21 hours at room temperature in the dark to allow for the partial reduction of disulfide bonds to form what is referred to subsequently as reduced protein. After the 21 hour incubation the contents of the vial was passed through a PD-10 desalting column, Pharmacia LKB Biotechnology, Piscataway, N.J.; the protein containing fraction was collected and the remaining eluate, which contained the stannous and other salts, was discarded. The reduced protein fraction was concentrated by ultrafiltration to a concentration of 1.7 mg/ml. 0.5 mg aliquots of reduced protein were placed in sealed, $N_2$ gas filled serum vials and frozen. 0.5 ml of 0.1 M $SnCl_2$ prepared in 40 mM potassium biphthalate/10 mM sodium tartrate solution, at pH 5.6, was added without allowing the reduced antibody solution to thaw, and this solution was also frozen. A sterile, 3 mm diameter tin metal shot was added, the vial flushed with $N_2$ and stored at minus 20° C. until needed for radiolabeling.

To radiolabel the gamma globulin preparation with Tc-99m, 1.0 ml of Sodium Pertechnetate-Tc-99m, U.S.P., containing 2.5 mCi of radioactivity, was added to the vial, and the vial and it's contents brought to room temperature, mixed and allowed to stand for 15 minutes. Thin layer chromatographic analysis of the product revealed that 99.6% of the radioactivity was protein bound. High performance liquid chromatography, using both UV and radioisotope detectors, showed that the Tc-99m elution paralleled the protein elution profile.

EXAMPLE II

This example illustrates the process of this invention for labeling monoclonal murine antibodies of IgG and IgM classes. The antibody was obtained from murine ascites or bioreactor fluid, purified to greater than 95%, and prepared at concentrations of greater than 1 mg/ml in 0.9% NaCl solution.

A stannous reducing solution was prepared as in Example I. Two whole antibody preparations were tested; B72.3, an IgG murine antibody, and anti-SSEA-1, an IgM murine antibody. Each antibody preparation was at a protein concentration of 1.7 mg/ml. To each ml of purified protein solution was added 0.66 ml of stannous reducing solution. The admixed solutions were placed in a sealed vial, the vial purged of oxygen with $N_2$ gas and placed in the dark at room temperature for 21 hours to permit partial reduction of disulfide bonds of the antibody protein. After the 21 hour incubation, the contents of each vial was passed through a PD-10 desalting column; the protein containing fraction was collected and the remaining eluate which contained the stannous and other salts was discarded. The reduced protein fraction was concentrated by ultrafiltration to a concentration of 2 mg/ml. Aliquots of reduced protein, containing from 0.5 to 2.0 mg protein, were placed in sealed, $N_2$ gas filled serum vials and frozen.

A pertechnetate reducing solution was prepared by dissolving 50 mg of gentisic acid, 0.375 mg $SnCl_2$ and 975 mg of sodium potassium tartrate in 50 ml of distilled water which had previously been deoxygenated by bubbling $N_2$ gas through it for two to three minutes. The pH was adjusted to 7.0 by addition of very dilute (0.05 N) NaOH. Equal volumes of this solution were layered over the frozen, reduced protein solution and this solution frozen. A sterile, 3mm diameter tin metal shot was added, the vial flushed with $N_2$ and stored at minus 20° C. until needed for radiolabeling.

To radiolabel the IgG or IgM preparations with Tc-99m, 1.0 ml of Sodium Pertechnetate-Tc-99m, U.S.P., containing 2.5 mCi of radioactivity, was added to each vial, and the vial and it's contents brought to room temperature, mixed and allowed to stand for 15 minutes. Thin layer chromatographic analysis of the products revealed that 90.0% to 96.5% of the radioactivity was protein bound. High performance liquid chromatography (HPLC), using both UV and radioisotope detectors, showed that the Tc-99m elution paralleled the protein elution profile. No non-protein bound radioactivity was found by HPLC analysis.

EXAMPLE III

This example illustrates the process of this invention for labeling F(ab')$_2$ fragment of a monoclonal antibody. This example also shows that the composition of the radiolabeled product varies with the method and type of disulfide reducing reagent used. This example also shows that the current method is superior to the original pretinning method of Crockford and Rhodes, U.S. Pat. No. 4,424,200 entitled "METHOD FOR RADIOLABELING PROTEINS WITH TECHNETIUM -99M", for this particular monoclonal antibody fragment. The F(ab')$_2$ fragment was obtained by pepsin digestion of murine monoclonal antibody followed by chromatographic purification which separated the F(ab')$_2$ fragments from other materials found in the pepsin digest with greater than 95% purity.

The monoclonal antibody fragment used in this example was obtained from Sorin Biotechnica, Italy. It is a murine anti-CEA F(ab')$_2$ which previous experimentation had shown radiolabeled with Tc-99m using the pretinning method very poorly. Four different radiolabeling procedures were employed; one used the original pretinning method described in U.S. Pat. No. 4,424,200, and the other three procedures used methods taught in this invention. The four procedures can be summarized as follows:

1. The original pretinning method described in U.S. Pat. No. 4,424,200, in which a pretinning solution was prepared as described in Example I, but no purification step was employed, and no pertechnetate reducing solution was added;

2. The method of this invention using stannous salt to reduce disulfide bonds in the antibody fragment, as described in Example I, including a purification step using a PD-10 desalting column, and a pertechnetate reducing solution composed of stannous salt with a tin pellet;

3. The method of this invention using 2-mercaptoethanol to reduce disulfide bonds in the antibody fragment. A 5% solution of 2-mercaptoethanol was prepared in 0.1 M phosphate buffer at pH 8.0. One ml of this solution was added to 1 mg of the lyophilized antibody fragment protein and mixed to dissolve. After 1 hour incubation at room temperature, 1.6 ml of saline was added and the partially reduced protein separated from the other components in the solution by passage through a PD-10 desalting column. The protein was concentrated by ultrafiltration to 1.7 mg/ml. A pertechnetate reducing solution composed of stannous salt with a tin pellet, as described in Example I, was then applied;

4. The method of this invention using dithiothreitol to reduce disulfide bonds in the antibody fragment. 15.4 mg of dl-dithiothreitol (DTT) was dissolved in 10 ml of a solution of 50 mM Tris and 1 mM EDTA at pH 8.0. For each mg of lyophilized protein to be reduced, 0.33 ml of the reducing solution was added with mixing to dissolve the protein. The reduction mixture was allow to react at 37° C. for one hour. The partially reduced protein was purified by size exclusion column chromatography with collection of the protein fraction corresponding to the molecular weight of the original F(ab')$_2$ antibody fragment. The chromatographically purified fragment was concentrated to 1.7 mg/ml in 0.9% saline by ultrafiltration. A pertechnetate reducing solution composed of stannous salt with a tin pellet, as described in Example I, was then applied.

For each of the four preparations, the frozen and vialed antibody fragment was radiolabeled and tested as described in Example I. The results of the four different procedures utilizing the same antibody fragment are listed in the following table.

TABLE 1

COMPARISON OF RESULTS USING DIFFERENT METHODS FOR PARTIAL REDUCTION OF THE DISULFIDE BONDS OF ANTI-CEA F(ab')$_2$

| Disulfide Reduction Method | Result |
|---|---|
| 1. Original pretinning U.S. Pat. No. 4,424,200 method | 4-9% of the Tc-99m bound to F(ab')$_2$; 45-53% bound to smaller fragments. |
| 2. This invention (Regulated Reduction) using Sn$^{-2}$ | 18-29% of the Tc-99m bound to F(ab')$_2$; 51-76% bound to smaller fragments. |
| 3. This invention (Regulated Reduction) using 2-mercaptoethanol | 79% of the Tc-99m bound to F(ab')$_2$; none bound to smaller fragments. |
| 4. This invention (Regulated Reduction) using DTT | 74% of the Tc-99m bound to F(ab')$_2$; none bound to smaller fragments. |

Table 1 shows that this specific F(ab')$_2$ murine monoclonal antibody fragment effectively fails to radiolabel using the original pretinning method taught in U.S. Pat. No. 4,424,200, in which there is no purification step and addition of limited amounts of pertechnetate reducing solution, yet effectively radiolabels using the regulated reduction method, particularly when an agent other than Sn+2 was used to reduce the disulfide bonds. The same sodium pertechnetate reducing agent, here Sn+2, was used in each procedure.

EXAMPLE IV

This example illustrates the process of this invention for labeling a monoclonal antibody which cannot be satisfactorily labeled by the original direct or pretinning method, or by other equivalent direct labeling methods. The reason for the failure of the previous direct methods with certain monoclonal antibodies is that during the reduction of the antibody either fragmentation or aggregation of the antibody occurs which results in protein species of altered molecular weight. An example of this is an anti-CEA murine monoclonal IgG provided by Sorin Biomedia, Italy. When this antibody is reduced with stannous salts, small amounts of fragments are formed which label preferentially with the reduced Tc-99m. When this antibody is reduced with dithiothreitol or 2-mercaptoethanol, dimers and polymers of reduced IgG are formed which label with Tc-99m. By the method of this invention, the antibody, after the disulfide bond reduction step, is purified by passage through a size exclusion chromatograph column. The column eluate corresponding only to the molecular weight of the original antibody was separated from both the smaller or larger protein species. A quantity of pertechnetate reducing solution sufficient to reduce the sodium pertechnetate but not to further reduce disulfide bonds in the antibody was added, and the antibody radiolabeled. The resulting Tc-99m labeled protein was of the correct molecular weight and free of the smaller or larger molecular weight contaminants.

The preceding examples can be repeated with similar success by substituting the generically or specifically described reactants and/or operating conditions of this invention for those used in the preceding examples. In particular, other proteins, chelating agents or substrates which contain disulfide bonds which can be reduced may be used in place of IgG, IgM and F(ab')$_2$ monoclonal antibody; other reducing agents can be used to reduce the disulfide bonds in the substance to be radiolabeled; other purification methods can be used to remove the reducing agent; other pertechnetate reducing agents can be used to reduce the sodium pertechnetate; and isotopes of rhenium can be used in addition to isotopes of technetium. The foregoing are merely illustrative, and other equivalent embodiments are possible and contemplated.

From the foregoing description, one skilled in the art can easily ascertain the essential characteristics of this invention and, without departing from the spirit and scope thereof, can make various changes and modifications of the invention to adapt it to various usages and conditions.

I claim:

1. A method of radiolabeling a protein containing disulfide bonds with a radionuclide selected from the group consisting of technetium and rhenium to obtain stable labeling, comprising the steps of:
   a) incubating the protein containing disulfide bonds with a first reducing agent, the period of incubation being sufficient to reduce available disulfide bonds to sulfhydryl groups while preventing excessive fragmentation of the protein;
   b) purifying the reduced protein to substantially remove the first reducing agent and impurities;
   c) adding a source of stannous ion agent to the reduced protein in a sufficient amount to reduce the radionuclide, the radionuclide to be added in a subsequent step;
   d) radiolabeling the purified reduced protein by adding the radionuclide, whereby the stannous ion agent reduces the radionuclide and the reduced radionuclide and reduced protein forms radionuclide-containing and sulfur-containing complexes.

2. The method of claim 1 wherein the radionuclide is technetium-99m in the form of sodium pertechnetate.

3. The method of claim 1 wherein the first reducing agent comprises at least one member selected from the group consisting of 2-mercaptoethanol; 1,4 dithiothreitol; 2,3 dihydroxybutane-1; 4 dithiol; 2-aminoethanethiol HCl; 2-mercaptoethylamine; thioglycolate; cyanide; and cysteine.

4. The method of claim 1 wherein the source of the stannous ion agent is present in a solution comprising alkali metal tartrate having a pH of between approximately 5.0 and 6.0.

5. The method of claim 1 wherein the source of the stannous ion agent comprises a member selected from the group consisting of stannous glucoheptonate, stannous gluconate and stannous phosphonate.

6. The method of claim 1 wherein the protein comprises a member selected from the group consisting of monoclonal antibodies, monoclonal antibody fragments and polyclonal antibodies.

7. The method of claim 1 wherein following step c), and prior to step d), the purified reduced protein with stannous ion agent is lyophilized in a vial, whereby the lyophilized purified reduced protein with stannous ion agent can be maintained for an indefinite period before radiolabeling in step d) by the addition of the radionuclide to the vial.

8. The method of claim 1 wherein following step b), and prior to step c), the purified reduced protein is frozen in a vial, and wherein following step c), and prior to step d), the stannous ion agent is frozen, whereby essentially no chemical reaction occurs between the frozen purified reduced protein and the stannous ion agent and the frozen purified reduced protein and stannous ion agent can be maintained for an indefinite period before radiolabeling in step d) by the addition of the radionuclide to the vial.

9. The method of claim 8 wherein following the freezing of the stannous ion agent the frozen purified reduced protein and frozen stannous ion agent are lyophilized.

10. A method of radiolabeling a protein containing disulfide bonds with a radionuclide selected from the group consisting of technetium and rhenium to obtain stable labeling, comprising the steps of:
   a) incubating the protein containing disulfide bonds with a source of stannous (II) ion, the period of incubation being sufficient to reduce available disulfide bonds to sulfhydryl groups while preventing excessive fragmentation of the protein;
   b) purifying the reduced protein to substantially remove stannous salts and impurities;
   c) adding a second Sn (II) agent to the purified reduced protein in a sufficient amount to reduce the radionuclide yet not significantly degrade the purified reduced protein, the radionuclide to be added in a subsequent step; and
   d) radiolabeling the reduced purified protein by adding the radionuclide, whereby the Sn (II) agents reduce the radionuclide and the reduced radionuclide forms radionuclide-containing and sulfur-containing complexes.

11. The method of claim 10 wherein the radionuclide is technetium-99m in the form of sodium pertechnetate.

12. The method of claim 10 wherein the source of the first Sn (II) agent is present in a solution comprising alkali metal tartrate having a pH of between approximately 5.0 and 6.0.

13. The method of claim 10 wherein the source of the second Sn (II) agent is present in a solution comprising alkali metal tartrate having a pH of between approximately 5.0 and 6.0.

14. The method of claim 10 wherein the source of the second Sn (II) agent comprises at least one member selected from the group consisting of stannous glucoheptonate, stannous gluconate and stannous phosphonate.

15. The method of claim 10 wherein the protein comprises a member selected from the group consisting of monoclonal antibodies, monoclonal antibody fragments and polyclonal antibodies.

16. The method of claim 10 wherein following step c), and prior to step d), the purified reduced protein with stannous ion agent is lyophilized in a vial, whereby the lyophilized purified reduced protein with stannous ion agent can be maintained for an indefinite period before radiolabeling in step d) by the addition of the radionuclide to the vial.

17. The method of claim 10 wherein following step b), and prior to step c), the purified reduced protein is frozen in a vial, and wherein following step c), and prior to step d), the stannous ion agent is frozen, whereby essentially no chemical reaction occurs between the frozen purified reduced protein and the stannous ion agent and the frozen purified reduced protein and stannous ion agent can be maintained for an indefinite period before radiolabeling in step d) by the addition of the radionuclide to the vial.

18. The method of claim 17 wherein following the freezing of the stannous ion agent the frozen purified reduced protein and frozen stannous ion agent are lyophilized.

* * * * *

UNITED STATES PATENT AND TRADEMARK OFFICE
CERTIFICATE OF CORRECTION

PATENT NO. : 5,078,985

DATED : January 7, 1992

INVENTOR(S) : Buck A. Rhodes

It is certified that error appears in the above-identified patent and that said Letters Patent is hereby corrected as shown below:

Column 1, line 31 of the Patent, change "4 or +5" to --+4 or +5--;

Column 1, line 56 of the Patent, change "Radioimmunotherapg" to --Radioimmunotherapy--;

Column 4, line 24 of the Patent, change "such as such as" to --such as--;

Column 4, line 61 of the Patent, change "2,3 dihydroxybutane-1, 4 dithiol" to --2,3-dihydroxybutane-1,4-dithiol--;

Column 6, line 17-18 of the Patent, change "2,3 dihydroxybutane-1, 4 dithiol" to --2,3-dihydroxybutane-1,4-dithiol--;

Column 8, line 55 of the Patent, delete the first occurrence of the word "obtained";

Column 9, line 30 of the Patent, change "it's" to --its--;

Column 11, line 10 of the Patent, change "allow" to --allowed--;

UNITED STATES PATENT AND TRADEMARK OFFICE
CERTIFICATE OF CORRECTION

PATENT NO. : 5,078,985

DATED : January 7, 1992

INVENTOR(S) : Buck A. Rhodes

It is certified that error appears in the above-indentified patent and that said Letters Patent is hereby corrected as shown below:

Column 11, line 64, of the patent change "Biomedia" to --Biotechnica --.

Signed and Sealed this

Eighth Day of February, 1994

*Attest:*

BRUCE LEHMAN

*Attesting Officer*    Commissioner of Patents and Trademarks